United States Patent [19]

Back

[11] 4,281,007
[45] Jul. 28, 1981

[54] METHOD OF STABILIZING SOIL-APPLIED DIMETHYLCARBAMYLTRIAZOLES

[75] Inventor: Gayle E. Back, Olathe, Kans.

[73] Assignee: Gulf Oil Corporation, Pittsburgh, Pa.

[21] Appl. No.: 891,985

[22] Filed: Mar. 31, 1978

[51] Int. Cl.³ ............................................. A01N 43/64
[52] U.S. Cl. ................................... 424/269; 548/262; 548/265
[58] Field of Search ................... 260/308 R; 424/269; 548/262, 265

[56] References Cited

U.S. PATENT DOCUMENTS

| | | |
|---|---|---|
| 2,832,716 | 4/1958 | Cassil et al. ................... 424/164 X |
| 2,927,882 | 3/1960 | Trademan et al. .............. 424/357 X |
| 3,794,661 | 2/1974 | Boehner et al. ................. 260/308 R |
| 4,054,664 | 10/1977 | Watkins et al. ..................... 424/269 |

*Primary Examiner*—Allen J. Robinson
*Attorney, Agent, or Firm*—Carl A. Cline

[57] ABSTRACT

Dimethylcarbamyltriazole insecticides of the type disclosed in U.S. Pat. Nos. 4,054,664 and 4,066,774 are stabilized against decarbamylation in the presence of clay minerals, either in the soil or in pesticide formulations by incorporating with the dimethylcarbamyltriazole at least one part by weight of nonionic aliphatic polyol per 10 parts of insecticide.

6 Claims, No Drawings

METHOD OF STABILIZING SOIL-APPLIED DIMETHYLCARBAMYLTRIAZOLES

DESCRIPTION OF THE INVENTION

A new class of insecticides and miticides, as disclosed in U.S. Pat. Nos. 4,054,664 and 4,066,774 are dimethylcarbamyl triazoles. Although these compounds are not carbamate esters, it is assumed that the insecticidal activity is attributable to the reaction of labile dimethylcarbamyl groups with specific enzymes, according to the accepted theory of the action of carbamate esters. The reactivity of the dimethylcarbamyl group, which is believed to be of critical importance with respect to utility is also the principal disadvantage when these compounds are formulated as granules with clays, or when applied to the soil to kill soil-borne insect pests. It has been discovered that exposure of the insecticides to finely divided argillaceous substances, such as various clays, causes the decarbamylation of the triazoles within a relatively short time at ordinary ambient temperatures. Some dimethylcarbamyltriazoles of the structural formula

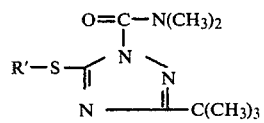

are particularly useful in combating insect larvae in the soil and as they are very toxic substances, it is more convenient to formulate these insecticides as clay-based granules of low concentration, containing five to ten percent active ingredients. In granular formulations of this type the insecticides will decompose at ambient or room temperature. The decomposition has been monitored by means of nuclear magnetic resonance and it has been found that the following reaction occurs:

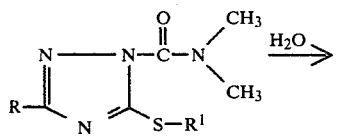

I have found that the addition of non-ionic aliphatic polyols to the clay granules stops the decarbamylation of the active ingredient, thereby stabilizing the material in the granular formulation.

The stabilizing effect has been demonstrated by the procedure described below.

PROCEDURE

The control sample was prepared by dissolving 5.0 g of active ingredient in acetone, then adding the resulting solution to 45.0 g of Florex clay granules. The acetone was evaporated, yielding a 10% formulation on clay. A sample was taken and analyzed by NMR. The remainder of the sample was placed in an oven at 50° C. Samples were taken at 1, 2, 4 and 8 week intervals.

The stabilized samples were prepared by dissolving the stabilizing agent in acetone, then adding the solution to the clay. The acetone was then removed and an acetone solution of the active ingredient was added to the clay. The acetone was then evaporated. A sample was taken and analyzed by NMR. The remainder of the material was placed in an oven at 50° C. Samples were taken at 1, 2, 4 and 8 week intervals.

The first table summarizes the results with the first of two triazoles, in which R is tert.butyl and $R^1$ is allyl, on different clays and additives stored in an oven at 50° C. The second table summarizes the results with a second triazole in which R is tert.butyl and $R^1$ is methyl. The third table summarizes the results when propylene glycol and active ingredient are added to the clay at the same time.

TABLE II

Triazole No. 2 (10% by wt. on clay)

| No. | Type Clay Carrier | Additive | % Product Remaining Time in Weeks at 50° C. | | | | |
|---|---|---|---|---|---|---|---|
| | | | 0 | 1 | 2 | 4 | 8 |
| 1 | Florex | None | 100 | 67 | 54 | 22 | — |
| 2 | Florex | 5% Propylene glycol | 100 | 100 | 100 | 100 | — |

TABLE I

Triazole No. 1 (10% by wt. on clay)

| No. | Type Clay Carrier | Additive (% by wt. of total composition) | % Product Remaining Time in Weeks at 50° C. | | | | |
|---|---|---|---|---|---|---|---|
| | | | 0 | 1 | 2 | 4 | 8 |
| 1 | Florex | None | 100 | 71 | 56 | 32 | 7 |
| 2 | Florex | 5% Propylene glycol | 100 | 100 | 100 | 100 | 100 |
| 3 | Florex | 4% Propylene glycol | 100 | 100 | 100 | 100 | 100 |
| 4 | Florex | 3% Propylene glycol | 100 | 100 | 100 | 100 | 100 |
| 5 | Florex | 2% Propylene glycol | 100 | 100 | 100 | 100 | 85 |
| 6 | Florex | 1% Propylene glycol | 100 | 100 | 84 | 66 | 54 |
| 7 | Bentonite | None | 100 | 89 | 83 | 82 | 81 |
| 8 | Bentonite | 5% Propylene glycol | 100 | 100 | 100 | 100 | 88 |
| 9 | Bentonite | 4% Propylene glycol | 100 | 100 | 100 | 100 | 89 |
| 10 | Bentonite | 3% Propylene glycol | 100 | 100 | 100 | 100 | 85 |
| 11 | Bentonite | 2% Propylene glycol | 100 | 100 | 100 | 100 | 88 |
| 12 | Bentonite | 1% Propylene glycol | 100 | 100 | 100 | 88 | 81 |
| 13 | Florex | 5% Maracarb N-1* | 100 | 100 | 100 | 81 | 67 |
| 14 | Florex | 5% Hexamethylenetetramine | 100 | 82 | 88 | 67 | 49 |
| 15 | Florex | 5% Pluronic L-44* | 100 | 100 | 100 | 100 | 100 |

TABLE I-continued

Triazole No. 1
(10% by wt. on clay)

| No. | Type Clay Carrier | Additive (% by wt. of total composition) | % Product Remaining Time in Weeks at 50° C. | | | | |
|---|---|---|---|---|---|---|---|
| | | | 0 | 1 | 2 | 4 | 8 |
| 16 | Florex | 5% 2-aminoethanol | 100 | 40 | 34 | 19 | 61 |
| 17 | Florex | 5% Ethylene glycol | 100 | 100 | 100 | 100 | 81 |
| 18 | Florex | 5% Tween 20* | 100 | 100 | 100 | 100 | 83 |
| 19 | Florex | 5% Urea | 100 | 100 | 100 | 85 | 72 |
| 20 | Florex | 5% $NH_3$ | 84 | 53 | 42 | 21 | 30 |

*Pluronic L-44 is a block copolymer resulting from condensing an average of 47 moles of ethylene oxide with a propylene oxide-propylene glycol condensation product.
Tween 20 is a product of condensation of an average of 20 moles of ethylene oxide with sorbitan monolaurate.
Maracarb N-1 is a salt of a low molecular weight lignosulfonic acid, containing some carbohydrate material.

TABLE III

Simultaneous Addition of Triazole and Polyol to Clay
(10% triazole by wt. on clay)

| No. | Type Clay Carrier | Triazole | Additive | % Product Remaining Time in Weeks at 50° C. | | | | |
|---|---|---|---|---|---|---|---|---|
| | | | | 0 | 1 | 2 | 4 | 8 |
| 1 | Florex | No. 1 | 5% Propylene glycol | 100 | 100 | 100 | 100 | 100 |
| 2 | Florex | No. 2 | 5% Propylene glycol | 100 | 100 | 100 | 100 | — |

I claim:

1. The method of improving the stability of a dimethylcarbamyltriazole pesticide against decarbamylation in contact with a finely divided argillaceous substance comprising incorporating therewith at least one part by weight of a non-ionic aliphatic polyol per ten parts by weight of dimethylcarbamyltriazole.

2. The method of claim 1 in which the argillaceous substance is clay and the non-ionic aliphatic polyol is propylene glycol.

3. The method of claim 1 in which the argillaceous substance is clay-containing soil and the dimethylcarbamyltriazole and non-ionic aliphatic polyol stabilizer are applied simultaneously.

4. The method of claim 1 in which the dimethylcarbamyltriazole pesticide and non-ionic aliphatic polyol are incorporated into clay-containing granular particles.

5. The method of claim 4 in which from one part to five parts by weight of propylene glycol are incorporated in the clay containing granular particles per ten parts by weight of dimethylcarbamyltriazole.

6. The stabilized granular pesticidal composition comprising clay, 10 percent by weight of a pesticide selected from 1-(N,N-dimethylcarbamyl)-3-tert.butyl-5-methylthio-1,2,4-triazole and 1-(N,N-dimethylcarbamyl)-3-tert.butyl-5-allylthio-1,2,4-triazole and from 1 percent to 5 percent by weight propylene glycol.

* * * * *